(12) United States Patent
Kwack et al.

(10) Patent No.: US 10,172,820 B2
(45) Date of Patent: Jan. 8, 2019

(54) SKIN PREPARATION COMPOSITION FOR EXTERNAL USE HAVING EXCELLENT ANTISEPTIC ABILITY

(71) Applicant: AMOREPACIFIC CORPORATION, Seoul (KR)

(72) Inventors: Il Young Kwack, Yongin-si (KR); Yu Na Yun, Yongin-si (KR); Tae Hun Park, Yongin-si (KR); Jin Sol Kim, Yongin-si (KR); Yun Hyeok Jung, Yongin-si (KR); Yeon Ju Hong, Yongin-si (KR); Kye Ho Shin, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 900 days.

(21) Appl. No.: 14/359,933

(22) PCT Filed: Nov. 23, 2012

(86) PCT No.: PCT/KR2012/009945
§ 371 (c)(1),
(2) Date: May 22, 2014

(87) PCT Pub. No.: WO2013/081331
PCT Pub. Date: Jun. 6, 2013

(65) Prior Publication Data
US 2014/0328953 A1 Nov. 6, 2014

(30) Foreign Application Priority Data
Nov. 28, 2011 (KR) .................. 10-2011-0124895

(51) Int. Cl.
| | | |
|---|---|---|
| *A61K 31/231* | (2006.01) | |
| *A61K 31/08* | (2006.01) | |
| *A61K 31/192* | (2006.01) | |
| *A61K 9/00* | (2006.01) | |
| *A61K 31/25* | (2006.01) | |
| *A61K 36/18* | (2006.01) | |
| *A61K 36/752* | (2006.01) | |
| *A61K 8/368* | (2006.01) | |
| *A61K 8/37* | (2006.01) | |
| *A61Q 17/00* | (2006.01) | |
| *A61K 8/97* | (2017.01) | |

(52) U.S. Cl.
CPC ............ *A61K 31/231* (2013.01); *A61K 8/368* (2013.01); *A61K 8/375* (2013.01); *A61K 8/97* (2013.01); *A61K 9/0014* (2013.01); *A61K 31/08* (2013.01); *A61K 31/192* (2013.01); *A61K 31/25* (2013.01); *A61K 36/18* (2013.01); *A61K 36/752* (2013.01); *A61Q 17/005* (2013.01)

(58) Field of Classification Search
None
See application file for complete search history.

(56) References Cited

U.S. PATENT DOCUMENTS

| | | |
|---|---|---|
| 6,432,908 B1 | 8/2002 | Dubief et al. |
| 6,589,519 B1 | 7/2003 | Restle et al. |
| 2008/0171031 A1* | 7/2008 | Jochim ............... A61K 8/0212 424/94.1 |
| 2010/0022660 A1* | 1/2010 | Wegner ................. A01N 25/16 514/724 |
| 2010/0048740 A1 | 2/2010 | Mercier et al. |

OTHER PUBLICATIONS

"Glyceryl undecylenate". From EWG's Skin Deep Cosmetics Database. Internet Archive Date: May 27, 2011 [Retrieved from the Internet on: Dec. 29, 2017]. Retrieved from: <URL: https://web.archive.org/web/20110527160451/https://www.ewg.org/skindeep/ingredient/719305/GLYCERYL_UNDECYLENATE/>.*
Marion Leschke, et al., "Boosting efficacy of preservatives", Personal Care, Preservatives, Sep. 2008, pp. 1-4.
Robert Miller, et al., "Bio-derived propanediol boosts preservative efficacy", Personal Care, Preservatives, US, May 2011, pp. 47-49.
International Searching Authority, International Search Report of PCT/KR2012/009945, dated Mar. 27, 2013.

* cited by examiner

*Primary Examiner* — Terry A McKelvey
*Assistant Examiner* — Catheryne Chen
(74) *Attorney, Agent, or Firm* — Sughrue Mion, PLLC

(57) ABSTRACT

The present invention relates to a skin preparation composition for external use having excellent antiseptic ability without using chemical antiseptics. More particularly, the present invention relates to a skin preparation composition for external use, comprising: glyceryl undecylenate having excellent antiseptic ability; and one or more mixtures of ethylhexylglycerin, glyceryl caprylate, p-anisic acid and a citrus mixed extract, thus improving antiseptic ability through the increased effects of antiseptic abilities of those materials.

3 Claims, 1 Drawing Sheet

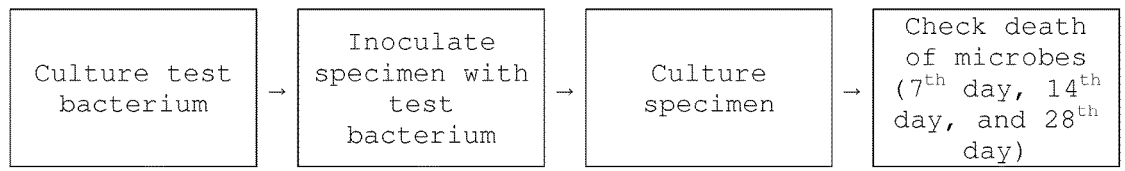

SKIN PREPARATION COMPOSITION FOR EXTERNAL USE HAVING EXCELLENT ANTISEPTIC ABILITY

TECHNICAL FIELD

The present invention relates to a skin preparation composition for external use having excellent antiseptic ability without using antiseptic chemicals and, more particularly to, a skin preparation composition for external use that contains a mixture comprising glyceryl undecylenate having excellent antiseptic ability, and at least one selected from the group consisting of ethylhexylglycerin, glyceryl caprylate, p-anisic acid, and a citrus mixed extract, thereby improving the antiseptic ability through the increased effects of the antiseptic ability of these substances.

BACKGROUND ART

The skin preparation composition for external use can be contaminated with contaminant microbes, such as by having the airborne microbes of the manufacturing plant, microbes contained in the preparation water or sticking to the material transfer pipes, the contact with the skin of the user, such as fingers, palms or the face during the use of the composition product, bacteria on the surface of the container of the composition product, or the introduction of foreign substances during the use of the composition product. For this reason, the skin preparation composition for external use may be mixed with antiseptic chemicals, such as paraoxy benzoic acid ester (parabens), imidazolidinyl urea, phenoxy ethanol, chlorophenesin, benzoic acid, sorbic acid, dehydroacetic acid, etc., for the purpose of suppressing the proliferation of the contaminant microbes and enhancing the antiseptic ability to kill the contaminant microbes. These antiseptic chemicals are excellent in effectiveness as an antiseptic means used in the skin preparation composition for external use but adversely lead to toxicity, skin irritations, irritability, allergies, and so forth. With all those problems, there is a need of reducing the use of antiseptic chemicals or developing a substitute for the antiseptic chemicals.

Recently, it becomes possible to prepare a skin preparation composition for external use without antiseptic chemicals or containing only a small amount of antiseptic chemicals less than the typical level of the antiseptic chemical level by using diols known to have antiseptic ability rather than the conventional antiseptic chemicals or packing the skin preparation composition in a container specifically designed to prevent introduction of contaminant microbes during the preparation process and suppressing the contamination with microbes. However, using diols may lead to taking the risk of affecting the safety concerning the skin irritations, solubilization, and the stability of emulsion type formulation. Further, the use of a container designed for supporting aseptic preparation or preventing introduction of microbes involves the complicated preparation process and increases the expenses for facility maintenance and containers, ending up having a lack in economical versatility.

DISCLOSURE OF INVENTION

Accordingly, the inventors of the present invention have studied to provide a skin preparation composition for external use that does not use the conventional antiseptic chemicals but has an antiseptic ability against externally introduced harmful microbes to the extent equivalent to or greater than the antiseptic ability of the skin preparation composition for external use containing antiseptic chemicals, and found out the fact that the use of glyceryl undecylenate mixed with ethylhexylglycerin, glyceryl caprylate, p-anisic acid, or a citrus mixed extract can offer excellent aseptic ability through the enhanced antiseptic effect of these substances, thereby completing the present invention.

It is therefore an object of the present invention to provide a skin preparation composition for external use having excellent antiseptic ability without using the conventional antiseptic chemicals.

To achieve the object of the present invention, there is provided a skin preparation composition for external use containing glyceryl undecylenate; and at least one selected from the group consisting of ethylhexylglycerin, glyceryl caprylate, p-anisic acid, and a citrus mixed extract.

The present invention does not use the conventional antiseptic chemicals but provides the antiseptic ability equivalent to or greater than the antiseptic ability of the composition using antiseptic chemicals. Further, it does not involve toxicity, skin irritations, irritability, allergies, or the like as caused by the use of antiseptic chemicals and thus can be used for the skin with safety.

BRIEF DESCRIPTION OF DRAWINGS

FIG. 1 is a flow chart showing the procedure for evaluating the antiseptic ability.

BEST MODES FOR CARRYING OUT THE INVENTION

The present invention is directed to a skin preparation composition for external use having excellent antiseptic ability by using a mixture of glyceryl undecylenate and at least one selected from the group consisting of ethylhexylglycerin, glyceryl caprylate, p-anisic acid, and a citrus mixed extract.

In the present invention, glyceryl undecylenate having an antibacterial effect is used in combination with ethylhexylglycerin, glyceryl caprylate, p-anisic acid, or a citrus mixed extract to achieve a great synergetic effect and thus provide excellent antiseptic ability with a small quantity. The composition of the present invention uses, with respect to the total weight of the composition, 0.01 to 4.0 wt. % of glyceryl undecylenate, 0.01 to 1.0 wt. % of ethylhexylglycerin, 0.01 to 1.0 wt. % of glyceryl caprylate, 0.01 to 1.0 wt. % of p-anisic acid, or 0.01 to 1.0 wt. % of a citrus mixed extract.

The citrus mixed extract used in the present invention is an extract from citrus plants. The citrus plants available for the citrus plant extract may include, but are not limited to, *Citrus Paradisi, Citrus Aurantium Bergamia, Citrus Aurantium Dulcis, Citrus Tangerina*, mandarin orange, or a mixture of these. In the present invention, the extract may be derived from any part of citrus plants, such as stems, leaves, flowers, fruits, and so forth, and is not limited to the extract of a specific part of citrus plants. Further, the extract may include not only the leachate obtained from citrus plants by leaching and decoction but also the concentrate obtained by concentrating part or the whole of the leachate or the dried one of the concentrate. Preferably, the extract thus obtained is mixed with vegetable glycerin. More specifically, the extract used in the present invention is obtained from the fruits, leaves, stems, or the like of citrus plants by compression, mixing, and fermentation. The fermentation product is subjected to centrifugal separation to collect a fermented extract in the liquid state, which is heat-treated and then mixed with vegetable glycerin.

In this manner, the present invention uses glyceryl undecylenate and ethylhexylglycerin, glyceryl caprylate, p-anisic acid, or a citrus mixed extract at an appropriate mixing ratio to provide a skin preparation composition for external use having sufficiently excellent antiseptic ability without adding antiseptic chemicals such as parabens or phenoxyethanol or the conventional diols possibly causing skin irritations or irritability.

Hereinafter, the disclosure of the present invention will be described in further detail with reference to examples and test examples, which are given for the understanding of the disclosure of the present invention and not intended to limit the scope of the claims in the present invention.

[Reference Example 1] Preparation of Example 1 and Comparative Examples 1 to 4

A lotion formulation is prepared by a general method according to the composition of the following Table 1 (unit: wt. %). In this regard, the citrus mixed extract is Bio Citro Liquid (Quinabra) commercially available, which includes *Citrus Paradisi* fruit extract, *Citrus Aurantium Bergamia* fruit extract, *Citrus Aurantium Dulcis* fruit extract, *Citrus Tangerina* fruit extract, and glycerin.

TABLE 1

| Ingredient | Example 1 | Example 2 | Example 3 | Example 4 | Comparative 1 | Comparative 2 | Comparative 3 | Comparative 4 | Comparative 5 | Comparative 6 | Comparative 7 |
| --- | --- | --- | --- | --- | --- | --- | --- | --- | --- | --- | --- |
| Purified water | Balance | Balance | Balance | Balance | Balance | Balance | Balance | Balance | Balance | Balance | Balance |
| Cyclopentasiloxane | 3.00 | 3.00 | 3.00 | 3.00 | 3.00 | 3.00 | 3.00 | 3.00 | 3.00 | 3.00 | 3.00 |
| Dipropylene glycol | 2.50 | 2.50 | 2.50 | 2.50 | 2.50 | 2.50 | 2.50 | 2.50 | 2.50 | 2.50 | 2.50 |
| Dimethicone/vinyl dimethicone cross polymer | 2.00 | 2.00 | 2.00 | 2.00 | 2.00 | 2.00 | 2.00 | 2.00 | 2.00 | 2.00 | 2.00 |
| Hydrolyzed wheat protein/PVP cross polymer | 2.00 | 2.00 | 2.00 | 2.00 | 2.00 | 2.00 | 2.00 | 2.00 | 2.00 | 2.00 | 2.00 |
| Beta-glucan | 1.30 | 1.30 | 1.30 | 1.30 | 1.30 | 1.30 | 1.30 | 1.30 | 1.30 | 1.30 | 1.30 |
| PEG-100 stearate | 1.20 | 1.20 | 1.20 | 1.20 | 1.20 | 1.20 | 1.20 | 1.20 | 1.20 | 1.20 | 1.20 |
| Cetyl ethyl hexanoate | 1.00 | 1.00 | 1.00 | 1.00 | 1.00 | 1.00 | 1.00 | 1.00 | 1.00 | 1.00 | 1.00 |
| Dimethicone | 1.00 | 1.00 | 1.00 | 1.00 | 1.00 | 1.00 | 1.00 | 1.00 | 1.00 | 1.00 | 1.00 |
| Cetearyl alcohol | 0.50 | 0.50 | 0.50 | 0.50 | 0.50 | 0.50 | 0.50 | 0.50 | 0.50 | 0.50 | 0.50 |
| Silica | 0.50 | 0.50 | 0.50 | 0.50 | 0.50 | 0.50 | 0.50 | 0.50 | 0.50 | 0.50 | 0.50 |
| Ammonium acryloyl dimethyl taurate/VP copolymer | 0.40 | 0.40 | 0.40 | 0.40 | 0.40 | 0.40 | 0.40 | 0.40 | 0.40 | 0.40 | 0.40 |
| Sorbitan sesquioleate | 0.30 | 0.30 | 0.30 | 0.30 | 0.30 | 0.30 | 0.30 | 0.30 | 0.30 | 0.30 | 0.30 |
| Carbomer | 0.15 | 0.15 | 0.15 | 0.15 | 0.15 | 0.15 | 0.15 | 0.15 | 0.15 | 0.15 | 0.15 |
| Triethanolamine | 0.14 | 0.14 | 0.14 | 0.14 | 0.14 | 0.14 | 0.14 | 0.14 | 0.14 | 0.14 | 0.14 |
| Disodium EDTA | 0.02 | 0.02 | 0.02 | 0.02 | 0.02 | 0.02 | 0.02 | 0.02 | 0.02 | 0.02 | 0.02 |
| Color | q.s. | q.s. | q.s. | q.s. | q.s. | q.s. | q.s. | q.s. | q.s. | q.s. | q.s. |
| Fragrance | q.s. | q.s. | q.s. | q.s. | q.s. | q.s. | q.s. | q.s. | q.s. | q.s. | q.s. |
| Glyceryl undecylenate | 0.5 | 0.5 | 0.5 | 0.5 | 1.00 | | | | | | |
| Ethylhexyl glycerin | 0.1 | | | | | | | 0.2 | | | |
| Glyceryl caprylate | | 0.2 | | | | | | | 0.4 | | |
| p-anisic acid | | | 0.2 | | | | | | 0.4 | | |
| Citrus mixed extract | | | | 0.2 | | | | | | 0.4 | |
| Methylparaben | | | | | | | | | | | 0.25 |
| Propylparaben | | | | | | | | | | | 0.1 |
| Phenoxyethanol | | | | | | | | | | | 0.4 |

[Test Example 1] Antiseptic Ability Test

The test is carried out according to the procedure as shown in FIG. 1 in order to evaluate the antiseptic ability.

A mixed microbial solution of *Escherichia coli* (ATCC8739), *Staphylococcus aureus* (ATCC6538), *Pseudomonas aeruginosa* (ATCC9027), *Candida albicans*

(ATCC10231), etc. is added to 20 to 30 g of each cosmetic composition of Examples 1 to 4 and Comparative Examples 1 to 7 removed of the initial microbes so that the initial concentration per specimen is $5 \times 10^5$ cfu (colony forming unit)/g. These bacteria are incubated in a thermostat at 32° C. for 4 weeks, during which 1 g of each cosmetic composition is taken on the $7^{th}$, $14^{th}$ and $28^{th}$ days to determine the viable count. The results are presented in Table 2.

As for fungi, a microbial solution of *Aspergillus niger* (ATCC16404) is added to 20 to 30 g of each cosmetic composition of Examples 1 to 4 and Comparative Examples 1 to 7 so that the initial concentration per specimen is $1 \times 10^5$ cfu (colony forming unit)/g. These fungi are incubated in a thermostat at 25° C., during which 1 g of each cosmetic composition is taken on the $7^{th}$, $14^{th}$ and $28^{th}$ days to determine the viable count and observe the appearance of mycelia and spores on the surface of each specimen over 8 weeks. The results are presented in Table 3.

As can be seen from Tables 2 and 3, compared to the comparative examples 2 to 6 each using glyceryl undecylenate, ethylhexyl glycerin, glyceryl caprylate, p-anisic acid, or a citrus mixed extract, the examples 1 to 4 according to the present invention had higher antiseptic ability even with the smaller amount of the ingredients. Even in comparison to the comparative example 7 using the conventional antiseptic chemicals, methylparaben, propylparabene and phenoxyethanol, the examples 1 to 4 showed higher antiseptic ability with the smaller amount of the ingredients.

[Test Examples 2] Usability (Irritability) Test

For fifteen panels sensitive to irritability like soreness or burning, the skin preparation compositions for external use according to the present invention in Examples 1 to 4 are compared with the skin preparation composition of Comparative Example 1. For this test, 0.5 ml of each test specimen of Comparative Example 1 and Example 1, Comparative Example 1 and Example 2, Comparative Example 1 and Example 3, or Comparative Example 1 and Example 4 is randomly applied to either side of the face to evaluate irritability, such as soreness, itching, and eye irritation. The results are presented in Table 4.

<Evaluation Criteria>
0-0.4: No irritation
0.4-1.0: Slight irritation
1.1-2.0: Mild irritation
2.1-3.0: Severe irritation

TABLE 2

| Cosmetic composition | | Bacteria (cfu/g) | | | |
|---|---|---|---|---|---|
| | | Initial viable count | $7^{th}$ day | $14^{th}$ day | $28^{th}$ day |
| Lotion | Example 1 | $5 \times 10^5$ | $<1 \times 10^3$ | $<1 \times 10^2$ | $<1 \times 10^2$ |
| | Example 2 | $5 \times 10^5$ | $<1 \times 10^3$ | $<1 \times 10^2$ | $<1 \times 10^2$ |
| | Example 3 | $5 \times 10^5$ | $<1 \times 10^3$ | $<1 \times 10^2$ | $<1 \times 10^2$ |
| | Example 4 | $5 \times 10^5$ | $<1 \times 10^3$ | $<1 \times 10^2$ | $<1 \times 10^2$ |
| | Comparative Example 1 | $5 \times 10^5$ | $>1 \times 10^6$ | $>1 \times 10^6$ | $>1 \times 10^6$ |
| | Comparative Example 2 | $5 \times 10^5$ | $5 \times 10^5$ | $3.1 \times 10^3$ | $1 \times 10^3$ |
| | Comparative Example 3 | $5 \times 10^5$ | $4.5 \times 10^5$ | $1 \times 10^5$ | $2 \times 10^3$ |
| | Comparative Example 4 | $5 \times 10^5$ | $3.5 \times 10^5$ | $1 \times 10^5$ | $3 \times 10^4$ |
| | Comparative Example 5 | $5 \times 10^5$ | $3.5 \times 10^5$ | $1 \times 10^5$ | $1 \times 10^4$ |
| | Comparative Example 6 | $5 \times 10^5$ | $4 \times 10^5$ | $4 \times 10^5$ | $4 \times 10^5$ |
| | Comparative Example 7 | $5 \times 10^5$ | $<1 \times 10^3$ | $<1 \times 10^2$ | $<1 \times 10^2$ |

TABLE 4

| | Usability Test Results (Irritability Score) | | |
|---|---|---|---|
| | Soreness | Burning | Average |
| Comparative Example 1 | 0.09 | 0.20 | 0.15 |
| Example 1 | 0.11 | 0.35 | 0.23 |
| Comparative Example 1 | 0.46 | 0.16 | 0.31 |
| Example 2 | 0.27 | 0.34 | 0.31 |

TABLE 3

| Cosmetic composition | | Fungi (cfu/g) | | | | |
|---|---|---|---|---|---|---|
| | | Initial viable count | $7^{th}$ day | $14^{th}$ day | $28^{th}$ day | Macroscopic observation |
| Lotion | Example 1 | $1 \times 10^5$ | $1 \times 10^4$ | $2 \times 10^2$ | $1 \times 10^2$ | None |
| | Example 2 | $1 \times 10^5$ | $1 \times 10^4$ | $2 \times 10^3$ | $1 \times 10^3$ | None |
| | Example 3 | $1 \times 10^5$ | $1 \times 10^4$ | $1 \times 10^3$ | $1 \times 10^2$ | None |
| | Example 4 | $1 \times 10^5$ | $1 \times 10^4$ | $1 \times 10^3$ | $1 \times 10^3$ | None |
| | Comparative Example 1 | $1 \times 10^5$ | $1 \times 10^5$ | $1 \times 10^5$ | $1 \times 10^5$ | Spores |
| | Comparative Example 2 | $1 \times 10^5$ | $2.3 \times 10^4$ | $3.6 \times 10^4$ | $1 \times 10^3$ | None |
| | Comparative Example 3 | $1 \times 10^5$ | $3 \times 10^4$ | $2.1 \times 10^4$ | $1 \times 10^3$ | None |
| | Comparative Example 4 | $1 \times 10^5$ | $3 \times 10^4$ | $2.1 \times 10^4$ | $1 \times 10^3$ | None |
| | Comparative Example 5 | $1 \times 10^5$ | $1 \times 10^3$ | $1 \times 10^2$ | $1 \times 10^2$ | None |
| | Comparative Example 6 | $1 \times 10^5$ | $1 \times 10^5$ | $1 \times 10^5$ | $1 \times 10^5$ | Spores |
| | Comparative Example 7 | $1 \times 10^5$ | $1 \times 10^4$ | $2 \times 10^3$ | $1 \times 10^3$ | None |

TABLE 4-continued

Usability Test Results (Irritability Score)

|  | Soreness | Burning | Average |
|---|---|---|---|
| Comparative Example 1 | 0.06 | 0.49 | 0.28 |
| Example 3 | 0.16 | 0.29 | 0.23 |
| Comparative Example 1 | 0.20 | 0.42 | 0.31 |
| Example 4 | 0.19 | 0.35 | 0.27 |

As can be seen from Table 4, the products using glyceryl undecylenate in combination with ethylhexylglycerin, glyceryl caprylate, p-anisic acid, or a citrus mixed extract has irritability at the level of no irritation and no significant difference in the irritability when compared to the product of Comparative Example 1 using none of the above-mentioned ingredients. This demonstrates that the ingredients used in the present invention causes no increase in the irritability.

[Test Example 3] Skin Irritation Test 40 panels are subjected to a patch test for 24 hours in order to evaluate the human skin safety of glyceryl undecylenate, ethylhexylglycerin, glyceryl caprylate, p-anisic acid, or a citrus mixed extract. The patch is applied to the upper part of the back of each panel, using 20 μL of the test ingredient on an IQ chamber (Chemotechique, Sweeden). The patch is removed after 24 hours of application and a first evaluation is conducted in 30 more minutes. After 24 hours, a second evaluation is carried out. To determine the severity of the skin irritation of each specimen, a weighted grade is applied according to the severity of the positive reaction on the skin to calculate the average skin irritation score as given by the following Equation and determine the severity of the skin irritation from the specimen.

$$\text{Average skin irritation score} = \frac{\sum \text{grade} \times \text{the number of panels with irritation} \times 100}{4(\text{maximum grade}) \times n(\text{total number of panels}) \times 2(\text{the nuber of visual scores})}$$ [Equation 1]

<Evaluation Criteria>
Score<1 (Grade I): No irritation
1≤Score<3 (Grade II): Slight irritation
3≤Score<5 (Grade III): Mild irritation
Score≥5: Severe irritation

TABLE 5

Test Results (n = 40)

| Test Ingredient | Score |
|---|---|
| Glyceryl undecylenate 4% | 0.00 |
| Ethylhexylglycerin 3% | 0.31 |
| Glyceryl caprylate 5% | 0.94 |
| p-anisic acid 1% | 0.94 |
| Citrus mixed extract 1% | 0.00 |

As can be seen from Table 5, all the ingredients, such as glyceryl undecylenate, ethylhexylglycerin, glyceryl caprylate, p-anisic acid, or a citrus mixed extract, cause almost no irritation.

Accordingly, the composition containing these ingredients when used as a topical formulation for skin application does not cause skin irritation and thus can be used with safety.

What is claimed is:

1. A composition for external use on skin, comprising a mixture of glyceryl undecylenate and ethylhexylglycerin a an effective antiseptic agent,
    wherein the content of glyceryl undecylenate is 0.01 to 4.0 wt. % with respect to the total weight of the composition, and
    wherein the content of ethylhexylglycerin is 0.01 to 1.0 wt. % with respect to the total weight of the composition.

2. The composition as claimed in claim 1, wherein the composition comprises, with respect to the total weight of the composition, 0.5 wt. % of glyceryl undecylenate and 0.01 wt. % of ethylhexylglycerin.

3. The composition as claimed in claim 1, wherein the composition is a cosmetic composition.

* * * * *